(12) United States Patent
Kumar et al.

(10) Patent No.: US 11,479,730 B1
(45) Date of Patent: Oct. 25, 2022

(54) PROCESS FOR INCREASING THE CONCENTRATION OF NORMAL HYDROCARBONS IN A STREAM

(71) Applicant: UOP LLC, Des Plaines, IL (US)

(72) Inventors: Manoj Kumar, Gurugram (IN); Mark P. Lapinski, Aurora, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 17/718,001

(22) Filed: Apr. 11, 2022

Related U.S. Application Data

(60) Provisional application No. 63/295,645, filed on Dec. 31, 2021.

(51) Int. Cl.
| | | |
|---|---|---|
| *C10G 11/00* | (2006.01) | |
| *C07C 7/09* | (2006.01) | |
| *C07C 4/06* | (2006.01) | |
| *B01D 3/14* | (2006.01) | |
| *C07C 7/00* | (2006.01) | |

(52) U.S. Cl.
CPC .............. *C10G 11/00* (2013.01); *B01D 3/143* (2013.01); *C07C 4/06* (2013.01); *C07C 7/005* (2013.01); *C07C 7/09* (2013.01); *C10G 2300/4018* (2013.01)

(58) Field of Classification Search
CPC ............ C10G 11/00; C10G 2300/4018; B01D 3/143; C07C 4/06; C07C 7/005; C07C 7/09
See application file for complete search history.

(56) References Cited

U.S. PATENT DOCUMENTS 3,630,885 A * 12/1971 Egan .................... C10G 65/043
208/66
2021/0277316 A1   9/2021 Funk

* cited by examiner

*Primary Examiner* — Thuan D Dang
(74) *Attorney, Agent, or Firm* — Paschall & Associates, LLC; Mark Goldberg

(57) ABSTRACT

A process increases the concentration of non normal paraffins in a feed stream comprising separating a naphtha feed stream into a normal paraffin rich stream and a non-normal paraffin rich stream. The non-normal paraffin rich stream is isomerized over an isomerization catalyst to convert non-normal paraffins to normal paraffins, hydrocrack C5+ hydrocarbon to C2-C4 paraffins and produce an isomerization effluent stream. The isomerization effluent stream is separated into a C3− off gas, C4 rich stream and C5+ stream that is recycled to the naphtha feed stream. A depentanizer column may be positioned to either remove C6+ from the naphtha feed stream or from a bottoms stream from a stabilizer column. The amount of C2-C4 paraffins that are provided is increased from about 55% to as much as 77% and even more with further modifications including operating at higher temperatures or increasing the volume of catalyst.

9 Claims, 3 Drawing Sheets

PROCESS FOR INCREASING THE CONCENTRATION OF NORMAL HYDROCARBONS IN A STREAM

This application claims priority from U.S. provisional application 63/295,645 filed on Dec. 31, 2021, which is incorporated herein in its entirety.

FIELD

The field is processes for increasing the concentration of non normal hydrocarbons in a feed stream and specifically separating out various fractions of a naphtha stream to convert iso-paraffins into normal paraffin and maximizing C2-C4 paraffins in an isomerization zone for producing a feed stream for a steam cracker.

BACKGROUND

Ethylene and propylene are important chemicals for use in the production of other useful materials, such as polyethylene and polypropylene. Polyethylene and polypropylene are two of the most common plastics found in use today and have a wide variety of uses. Uses for ethylene and propylene include the production of vinyl chloride, ethylene oxide, ethylbenzene and alcohol.

The great bulk of the ethylene consumed in the production of the plastics and petrochemicals such as polyethylene is produced by the thermal cracking of higher molecular weight hydrocarbons. Steam is usually mixed with the feed stream to the cracking reactor to reduce the hydrocarbon partial pressure and enhance olefin yield and to reduce the formation and deposition of carbonaceous material in the cracking reactors. The process is therefore often referred to a steam cracking or pyrolysis.

The composition of the feed to the steam cracking reactor affects the product distribution. A fundamental basis of this is the propensity of some hydrocarbons to crack more easily than others. The normal ranking of tendency of the hydrocarbons to crack to ethylene is normally given as normal paraffins, iso-paraffins, olefins, naphthenes, and aromatics. Benzene and other aromatics are particularly resistant to steam cracking and undesirable as cracking feed stocks, with only the alkyl side chains being cracked to produce the desired product.

The feed to a steam cracking unit is also normally a mixture of hydrocarbons varying both by type of hydrocarbon and carbon number. This variety makes it difficult to separate less desirable feed components, such as naphthenes and aromatics, from the feed stream by fractional distillation. The normal paraffins and the non-normal paraffins can be separated by fractionation or an adsorption process. Increasing the concentration of normal paraffins in a stream can improve the quality of a feedstock to the steam cracking unit.

Common feeds to steam crackers include light naphtha, which is concentrated in C5-C6 hydrocarbons, and LPG, which comprises C3-C4 hydrocarbons. Light naphtha streams typically contain a mixture of n-paraffins, iso-paraffins, naphthenes and aromatics. It is generally not possible to procure light naphtha streams that are concentrated in n-paraffins. Similarly, LPG streams typically contain a mixture of n-butane, iso-butane, and propane, but streams concentrated in n-butane are not commonly available.

One way to upgrade light naphtha is first to separate the naphtha into a normal paraffin rich stream and a non-normal paraffin rich stream; and subsequently convert a substantial amount of the non-normal paraffin stream in an isomerization zone in the presence of a catalyst into normal paraffins.

It has been found that prior art processes for such conversion of non-normal paraffins to normal paraffins result in about a 55% yield of C2, C3 and C4 paraffins and about 44% of the C5+ hydrocarbons are in a bottom stream from a stabilizer to be sent directly to the steam cracker.

An efficient process for separating and converting the iso-paraffins in light naphtha to normal paraffins with an increased yield of C2, C3 and normal C4 paraffins including utilizing the C5+ hydrocarbons and a would significantly increase the profitability of steam cracking operations by increasing the yield of high value ethylene and propylene.

BRIEF SUMMARY

A process is provided for increasing the concentration of non-normal paraffins in a feed stream comprising sending the feed stream to an isomerization reactor over a catalyst to convert non-normal paraffins to normal paraffins. The reaction conditions include a temperature of at least 390° F. to crack a portion of C5 paraffins in the feed stream to C2-C4 paraffins and to produce an effluent stream comprising C2-C5 and some C6+ hydrocarbons. The effluent stream is separated into a C3− off gas stream, a C4 rich stream and a C5+ recycle stream and the C5+ recycle stream to said feed stream. There may be further processing to separate a C6+ purge stream from the C5+ recycle stream. The feed stream may be sent to a depentanizer column before being sent to the isomerization reactor in which the depentanizer column separates the feed stream into a C5 rich stream to be sent to the isomerization reactors and a C6+ stream to be sent outside of the process. In an alternative embodiment, the C5+ recycle stream may be sent to a depentanizer column to be separated into a C5 recycle stream to be combined with the feed stream and a C6+ purge stream that is separated from the process. In a lower temperature and lower space velocity embodiment, the isomerization reactor is operated at a temperature from about 390-400 F. Under these conditions the effluent comprises from about 56-77% C2-C4 paraffins. In another embodiment, the isomerization reactor is operated at a higher temperature from about 410-425 F. The higher temperatures result in an improved yield of about 75-87 wt % C2-C4 paraffins. The combination of the recycling of the C5+ and the higher temperatures can lead to essentially all of the C5 paraffins being cracked to C2-C4.

Another feature of the disclosure is that an increased volume of catalyst may be used to obtain a higher yield. In the examples, the reactors contain between a base amount of catalyst up to 1.35 times as much catalyst as the base amount. While in the base case the yield is about 56 wt % C2-C4 paraffins, at the increased catalyst volume with higher temperatures, a yield up to 87% was obtained. When the process is to be operated at the higher temperature.

The C3-off gas stream may be further separated into a C2− off gas stream and a C3 stream which can be sent to a propane dehydrogenation process. In the process, the reactors are isomerization reactors operated under conditions to convert non normal paraffins to normal paraffins and to crack C5 paraffins to C2-C4 paraffins.

Additional details and embodiments of the invention will become apparent from the following detailed description of the invention.

BRIEF DESCRIPTION OF THE DRAWINGS

The figures provide schematic views of a conversion unit.

DESCRIPTION OF THE INVENTION

Figure 1:
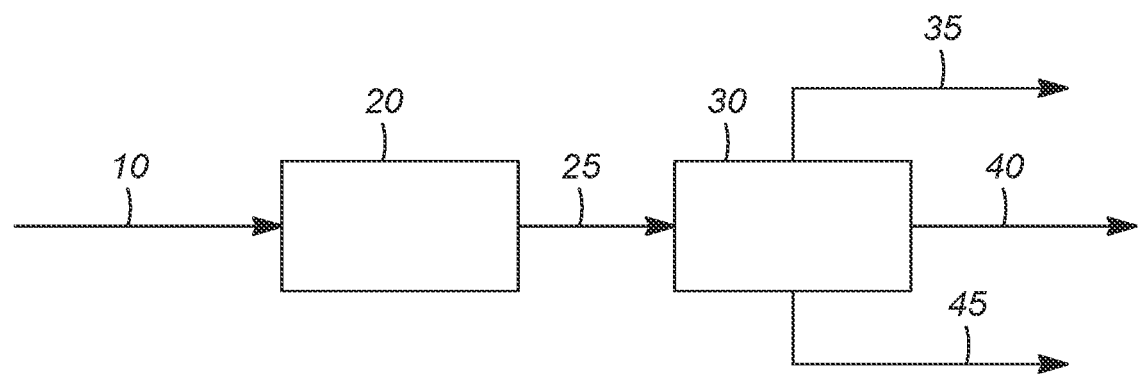
FIG. 1 is a base case of a schematic to convert a stream containing non-normal paraffins to normal paraffins.

The present disclosure endeavors to separate normal paraffins from a light naphtha stream for ideal steam cracker feed. The process employs a normal paraffin-non-normal hydrocarbon separation to extract normal paraffins from the light naphtha stream and transports the normal paraffins to a steam cracking unit. Furthermore, the non-normal hydrocarbons are converted to normal paraffins and transported to a steam cracking unit. The non-normal hydrocarbons, which include iso-paraffins, naphthenes and aromatics, can optionally undergo an additional separation to remove the C6 cyclics and any C7+ components from the C5 and C6 iso-paraffins. The C6 cyclics include methylcyclopentane (MCP), cyclohexane and benzene. The C5 and C6 iso-paraffins can be isomerized to increase the concentration of normal paraffins and then subjected to separation. The C5+ paraffins can be recycled back to the normal-non-normal separation while C4 hydrocarbons can be further separated to remove normal C4 paraffins for feed to the steam cracking unit. The C2-C3 paraffins can be directly sent to the steam cracker unit. Separated iso-C4 paraffins can be reverse isomerized to equilibrium concentrations of normal-C4 paraffins which can be removed and forwarded to the steam cracking unit.

In the explanation herein, there will generally be discussed a system with a single reactor for representation purposes. However, there may be 1-5 reactors in a contemplated flow scheme. Preferably there are 3 or 4 reactors in a standard operating configuration and 5 reactors in a high temperature configuration. Operating temperatures have been found to be a key parameter in the process with higher operating temperatures resulting in higher yield. Under one model using current operating temperatures the yield ranges from up to 65.4% with a base amount of catalyst in the reactor with can improve further up to 77.0% with higher catalyst volumes that may be up to 21% greater than base case. The results at even higher temperatures can increase the yield to 86.9% but it is necessary to spread the same catalyst volume over 5 reactors to manage the heat load at these higher temperatures.

A further improvement that is provided herein is that the C5 materials are essentially completely processed to C2, C3 and C4 by being recycled to the isomerization reactor and by being hydrocracked to C2, C3 and C4. The C2 and C3 production in the isomerization reactor is especially useful for the downstream steam cracker to maximize ethylene and propylene yield. A further improvement in yield is provided by limiting the amount of C6 going to the isomerization reactor so that C6+ stream is either purged or separated in a depentanizer column. A resulting C4 rich stream will have a mixture of normal and non-normal paraffins in equilibrium (at about a 40:60 ratio) and will be further processed in a separate reverse isomerization reactor to convert non normal C4 to normal C4.

The term "$C_x$" is to be understood to refer to molecules having the number of carbon atoms represented by the subscript "x". Similarly, the term "$C_x-$" refers to molecules that contain less than or equal to x and preferably x and less carbon atoms. The term "$C_x+$" refers to molecules with more than or equal to x and preferably x and more carbon atoms.

The naphtha feed stream is preferably a hydrotreated light naphtha stream comprising substantially C5 and C6 hydrocarbons having a T90 between about (50° C.) and about 90° C. The end point is taken to minimize the presence of hydrocarbons with more than six carbon atoms in the feed. No more than about 10 wt % C7+ hydrocarbons, preferably no more than about 2 wt % C7+ hydrocarbons can be present in the light naphtha feed stream. The naphtha feed stream may comprise normal paraffins, iso-paraffins, naphthenes, and aromatics.

It is also understood from the fundamentals that normal paraffins are more prone to crack to olefins than non-normal paraffins in a steam cracking unit. It is also understood that the lighter hydrocarbons, C2 and C3, in the feed to the steam cracker are equally good and results in higher olefin yields. We have found that the C5 rich stream is preferred for isomerization reactor resulting in higher C2-C4 yield and minimum side reactions. Hence, it is desired to increase the concentration of non normal C5 paraffins in the isomerization reactor feed stream 26. Several steps are taken in the process to increase the concentration of the non normal C5 paraffins in isomerization reactor feed increase the concentration of C2, C3 and C4 paraffins in the isomerization reactor effluent stream.

As used herein, the term "a component-rich stream" means that the rich stream coming out of a vessel has a greater concentration of the component than the feed to the vessel. As used herein, the term "a component-lean stream" means that the lean stream coming out of a vessel has a smaller concentration of the component than the feed to the vessel.

A feed stream may first undergo some separations into normal and non-normal paraffins as well as separation into C5 rich stream and C6+.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

A non-normal paraffin rich stream particularly rich in non-normal C4, C5 and C6 paraffins can be isomerized to increase the concentration of normal C4, C5 and C6 paraffins to equilibrium levels. However, it has been discovered that the conversion to normal paraffins in an isomerization zone can be increased by removing a portion of the C6 cyclic hydrocarbons, such as cyclohexane, methylcyclopentane, and benzene, in the isomerization feed stream passing into the isomerization zone. Specifically, when the concentration of C6 cyclic hydrocarbons in the stream has been reduced, disproportionation reactions occur which lead to increased amounts of valuable C2, C3 and C4 paraffins, as well as increases in the per pass conversion of the iso-paraffin hydrocarbons in the feed to normal paraffins. The products from the disproportionation reactions undergo isomerization reactions leading to an increase in yields of normal paraffins. Furthermore, additional conversion to C2 to C4 normal paraffins in the non-normal paraffin rich stream is accomplished via hydrocracking reactions.

In a base case shown in FIG. 1, a fresh feed 10 is sent to an isomerization zone 20 to be converted from non-normal to normal paraffins. The effluent 25 is then sent to a stabilizer column 30 to be separated into an off-gas 35 comprising C3- from the top of stabilizer column, a C4 rich stream 40 to be sent to be converted to normal paraffins and a C5+ stream that is purged.

Figure 2:
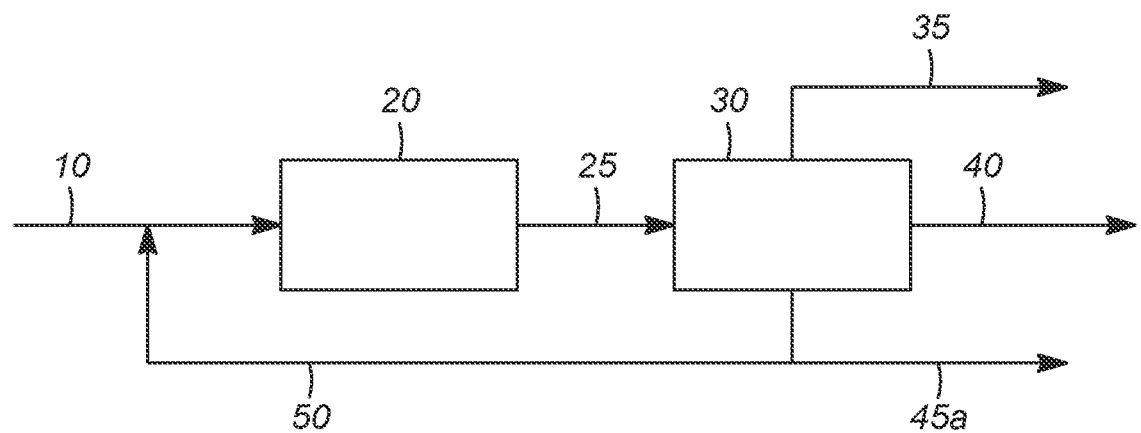
FIG. 2 provides a schematic of a process in which a portion of the heavier hydrocarbons are recycled to be converted to normal hydrocarbons.

In an embodiment of the invention shown in FIG. 2, a portion of the C5+ stream is recycled to be sent through isomerization zone. More specifically, a fresh feed 10 is sent to an isomerization zone 20 to be converted from non-normal to normal paraffins. The effluent 25 is then sent to a stabilizer column 30 to be separated into an off-gas 35 comprising C3- from the top of stabilizer column, a C4 rich stream 40 to be sent to be converted to normal paraffins and C5+ stream that is divided into a first portion 45a that is purged to minimize accumulation of C6+ material in feed to isomerization and a second portion 50 that is recycled to be combined with fresh feed 10.

Figure 3:
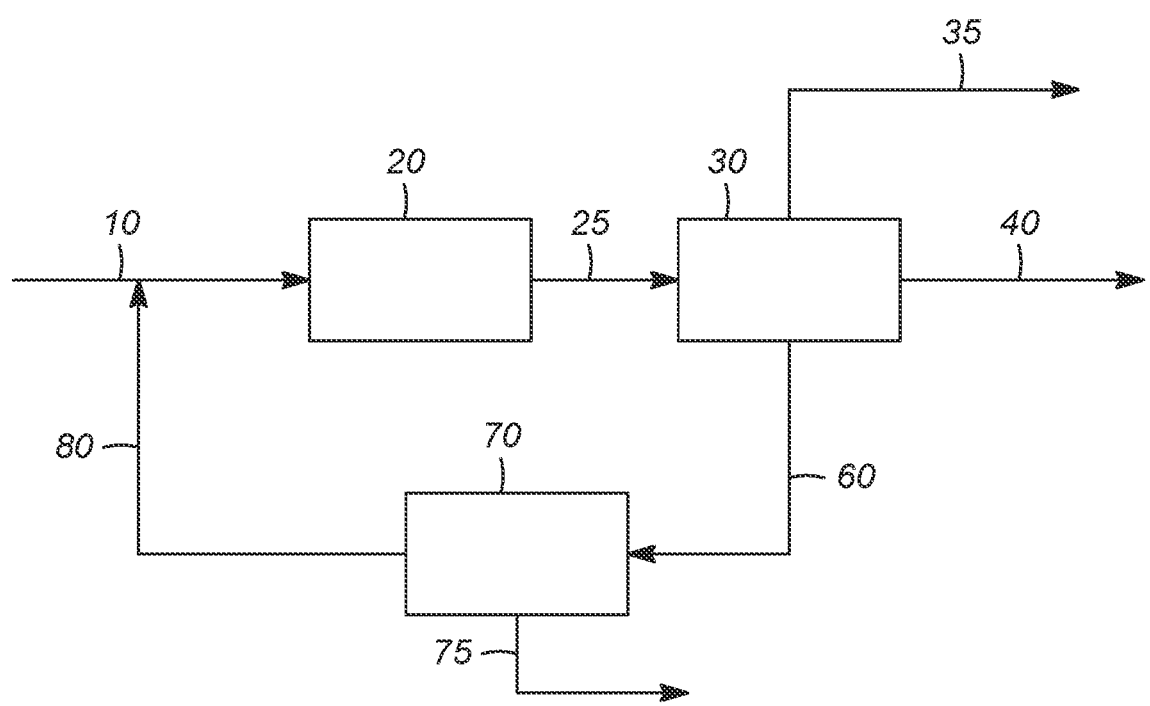
FIG. 3 shows a schematic of the process in which a depentanizer column is added to the flow scheme.

FIG. 3 shows an embodiment of the disclosure in which a depentanizer column is used on the heavier liquid hydrocarbon stream exiting the stabilizer column. More specifically, a fresh feed 10 is sent to an isomerization zone 20 to be converted from non-normal to normal paraffins. The effluent 25 is then sent to a stabilizer column 30 to be separated into an off-gas C3- stream 35, a C4 rich stream 40 to be sent to be converted to normal paraffins and a stream 60 of heavier liquid hydrocarbons including C5+ that is sent to depentanizer column 70 to separate C5 recycle stream 80 and C6+ stream 75.

Figure 4:
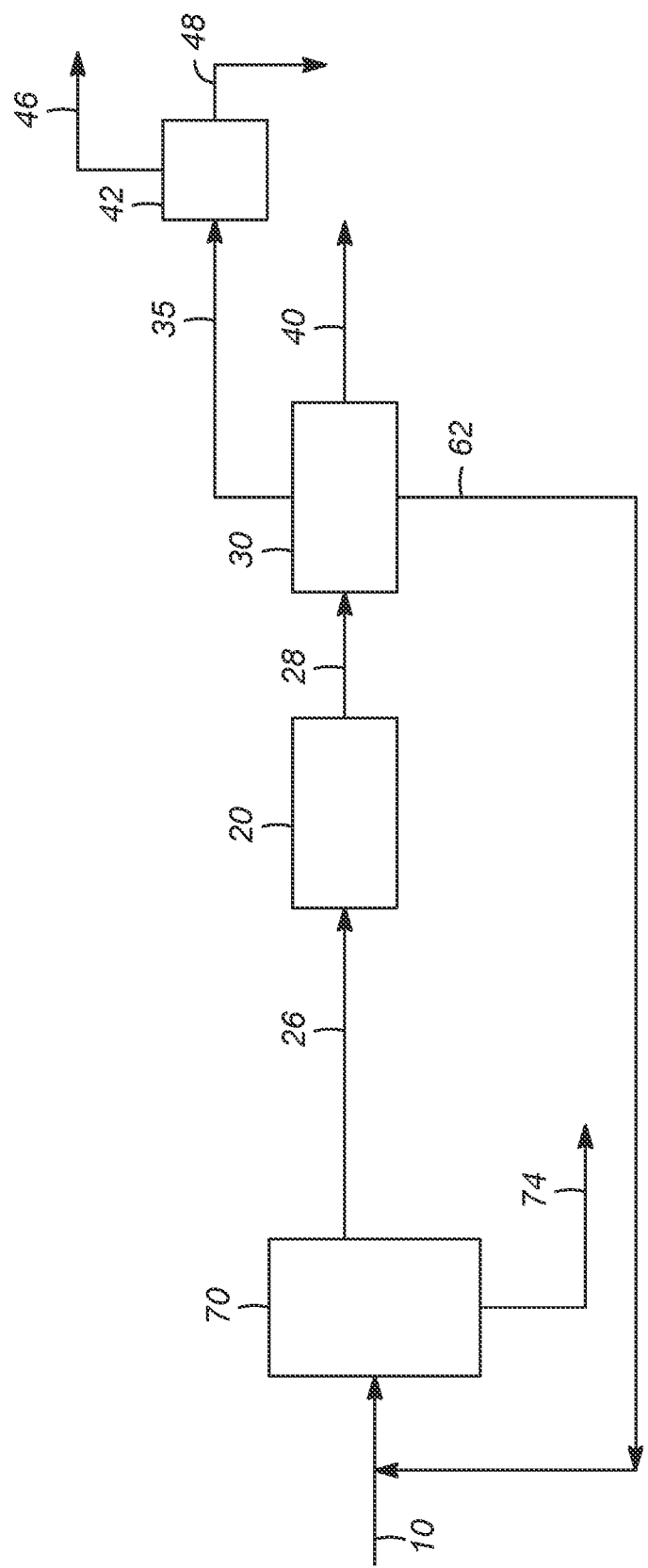
FIG. 4 shows a variation of the process in which the C5+ stream is recycled to be combined with feed stream.

FIG. 4 shows an embodiment in which a hydrotreated naphtha stream 10 is first sent to depentanizer column 70 to be divided into a C5 rich feed 26 and a C6+ stream 74 of hydrotreated naphtha. C5 rich feed 26 is sent to isomerization zone 20 to produce effluent 28 that is sent to stabilizer column 30 to be separated into C5+ recycle stream 62 that is combined with hydrotreated naphtha stream 10. In addition are shown C4 rich draw 40 and C3- off gas stream 35 which is then separated by separator 42 into C2- off gas stream 46 and a C3 stream 48 that can be sent to be further processed.

The isomerization catalyst in the isomerization unit 20 may include chlorided alumina, sulfated zirconia, tungstated zirconia or zeolite-containing isomerization catalysts. The higher isomerization catalyst may be amorphous, e.g., based upon amorphous alumina, or zeolitic. A zeolitic catalyst would still normally contain an amorphous binder. The catalyst may comprise a sulfated zirconia and platinum as described in U.S. Pat. No. 5,036,035 and European patent application 0 666 109 A1 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. These documents are incorporated herein for their teaching as to catalyst compositions, isomerization operating conditions and techniques. An advantage of a non-chlorided catalyst, such as a sulfated zirconia catalyst, is the absence of chloride omitting further treatment of the effluent streams from the isomerization unit 20. If chlorided alumina catalyst is used as the isomerization catalyst, a chloriding agent will be added.

The isomerization process conditions in the isomerization unit include an average reactor temperature usually ranging from about 40° to about 250° C. A preferred reactor temperature is about 205° C. In an embodiment in which an improved yield is provided, the reactor temperature is between about 210-218° C. Reactor operating pressures generally range from about 100 kPa to 10 MPa absolute. Liquid hourly space velocities (LHSV) range from about 0.2 to about 25 volumes of hydrocarbon feed per hour per volume of catalyst. Hydrogen is admixed with or remains with the higher isomerization feed to the higher isomerization unit to provide a mole ratio of hydrogen to hydrocarbon feed of from about 0.01 to 20. The hydrogen may be supplied totally from outside the process or supplemented by hydrogen recycled to the feed after separation from higher isomerization reactor effluent.

Contacting within the isomerization unit 20 may be effected using the isomerization catalyst in a fixed-bed system, a moving-bed system, a fluidized-bed system, or in a batch-type operation. The reactants may be contacted with the bed of higher isomerization catalyst particles in upward, downward, or radial-flow fashion. The reactants may be in the liquid phase, a mixed liquid-vapor phase, or a vapor phase when contacted with the higher catalyst particles, with a mixed phase or vapor phase being preferred. The higher isomerization unit 20 may be in a single reactor or in up to five reactors with suitable means therebetween to ensure that the desired isomerization temperature is maintained at the entrance to each zone.

A comparison was made as shown in Table 1 of the effect on yield of C2-C4 product based on the number of reactors, the space velocity and the temperature in the reactor. It was found that increasing the catalyst volume from a base volume up to 33% more increased the yield as did increasing the temperature in the reactor from the range of about 390-400° F. up to 410-425° F. The higher temperature was for a system having 5 reactors instead of the 3 reactors in the other examples.

TABLE 1

| 1 Low Severity (Fixed Catalyst Volume) | | | |
| --- | --- | --- | --- |
| | BASE Case (FIG. 1) | FIG. 2 Flow Scheme | FIG 3 or 4 Flow Scheme |
| No. Of Reactors | 3 | 3 | 3 | 4 |
| Cat Vol | BASE | BASE | BASE | BASE |
| LHSV | BASE | 1.50 × BASE | 1.70 × BASE | 1.70 × BASE |
| Rx Temp, deg F. | 390-400 | 390-400 | 390-400 | 390-400 |
| C2-C4 yield wt % | 56.6 | 61.3 | 64.1 | 65.4 |

| 2 Low Severity (Fixed LHSV) | | | |
| --- | --- | --- | --- |
| | BASE Case (FIG. 1) | FIG. 2 Flow Scheme | FIG. 3 or 4 Flow Scheme |
| No. Of Reactors | 3 | 3 | 3 | 4 |
| Cat Vol | BASE | 1.33 × BASE | 1.33 × BASE | 1.33 × BASE |
| LHSV | BASE | BASE | BASE | BASE |
| Rx Temp, deg F. | 390-400 | 390-400 | 390-400 | 390-400 |
| C2-C4 yield wt % | 56.6 | 74.3 | 75.0 | 77.0 |

| 3 High Severity Design (Fixed LHSV) | | |
| --- | --- | --- |
| | BASE Case | FIG. 3 or 4 Flow Scheme |
| No. Of Reactors | 5 | 5 |
| LHSV | BASE | BASE |
| Rx Temp, deg F. | 410-425 | 410-425 |
| C2-C4 yield wt % | 75.9 | 86.9 |

The invention claimed is:

1. A process for increasing the concentration of normal paraffins in a feed stream comprising non-normal paraffins comprising:

sending said feed stream comprising non-normal paraffins to an isomerization reactor containing a catalyst at a temperature of from at least 390° F. to convert non-normal paraffins to normal paraffins and to crack a portion of $C_5$ paraffins to $C_2$-$C_4$ paraffins to produce an effluent stream comprising $C_2$-$C_5$ hydrocarbons and some C6+ hydrocarbons;

separating said effluent stream into a C3− off gas stream comprising $C_2$ and $C_3$ paraffins, a C4 rich stream and a C5+ recycle stream;

sending the C3-off gas stream comprising $C_2$ and $C_3$ paraffins to a steam cracker unit to convert $C_2$ and $C_3$ paraffins to ethylene and propylene;

separating a purge stream comprising C6+ from the C5+ recycle stream to produce a C5 recycle stream; and recycling said C5 recycle stream to said feed stream.

2. The process of claim 1 wherein said feed stream is sent to a depentanizer column before being sent to said isomerization reactor wherein said depentanizer column separates said feed stream into a C5 rich stream to be sent to said isomerization reactor and a C6+ stream to be sent outside of said process.

3. The process of claim 1 wherein said C5+ recycle stream is sent to a depentanizer column to be separated into said C5 recycle stream to be combined with said feed stream and said C6+ purge stream that is separated from said process.

4. The process of claim 1 wherein said isomerization reactor are operated at a temperature from about 390-400° F.

5. The process of claim 4 wherein said effluent comprises from about 56-77% C2-C4 paraffins.

6. The process of claim 1 wherein said isomerization reactor is operated at a temperature from about 410-425 F.

7. The process of claim 6 wherein said effluent comprises from about 75-87 wt % C2-C4 paraffins.

8. The process of claim 1 wherein essentially all of said C5+ paraffins are cracked to C2-C4.

9. The process of claim 1 wherein said effluent stream comprises from about 56-87 wt % C2-C4 paraffins.

* * * * *